United States Patent [19]

Katsube et al.

[11] 4,169,146
[45] Sep. 25, 1979

[54] NOVEL MORPHOLINE DERIVATIVES AND TREATING DEPRESSION THEREWITH

[75] Inventors: Junki Katsube, Toyonaka; Atsuyuki Kojima, Nishinomiya; Makoto Sunagawa, Toyonaka; Yoshinori Takashima, Nishinomiya; Yoshito Kameno, Minoo; Hisao Yamamoto, Kobe, all of Japan

[73] Assignee: Sumitomo Chemical Company, Limited, Osaka, Japan

[21] Appl. No.: 811,944

[22] Filed: Jun. 30, 1977

Related U.S. Application Data

[62] Division of Ser. No. 646,908, Jan. 6, 1976, Pat. No. 4,085,210.

[30] Foreign Application Priority Data

Jun. 1, 1975 [JP] Japan .................................. 50-4540
Jun. 4, 1975 [JP] Japan .................................. 50-67767

[51] Int. Cl.² .............................................. A61K 27/00
[52] U.S. Cl. ........................ 424/248.4; 424/248.5 F; 544/154
[58] Field of Search .................. 424/248.4, 248.57; 544/154

[56] References Cited

U.S. PATENT DOCUMENTS

4,085,210  4/1978  Katsube et al. .................. 544/154

Primary Examiner—Stanley J. Friedman
Attorney, Agent, or Firm—Birch, Stewart, Kolasch and Birch

[57] ABSTRACT

Novel morpholine compounds of the formula:

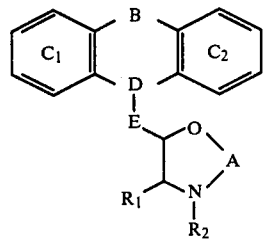

wherein $R_1$ represents hydrogen or $C_1$-$C_4$ alkyl, $R_2$ represents hydrogen, $C_1$-$C_4$ alkyl, $C_3$-$C_5$ alkenyl, $C_3$-$C_5$ alkynyl, aryl-($C_1$-$C_4$)alkyl, ($C_3$-$C_6$)cycloalkyl($C_1$-$C_4$)alkyl, polyhalo($C_2$-$C_4$) alkyl or hydroxy($C_2$-$C_4$)alkyl, A represents straight or branched $C_2$-$C_4$ alkylene, B represents a divalent radical selected from the group consisting of —$CH_2$—$CH_2$—, —CH=CH—,

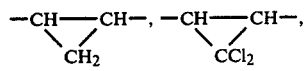

—$CH_2$—O—, —$CH_2$—S—, —S— and —O—, >D—E— represents a trivalent radical selected from the group consisting of >CH—$CH_2$— and >C=CH— and $C_1$ and $C_2$ each represent 1,2-phenylene optionally substituted with one or more substituents selected from the group consisting of halogen, $C_1$-$C_4$ alkyl and $C_1$-$C_4$ alkoxy, and their non-toxic salts, which are useful as antidepressants and can be produced by various methods.

10 Claims, No Drawings

NOVEL MORPHOLINE DERIVATIVES AND TREATING DEPRESSION THEREWITH

This application is a divisional of copending application Ser. No. 646,908, filed on Jan. 6, 1976, now U.S. Pat. No. 4,085,210.

The present invention relates to novel morpholine derivatives and their production and use.

The novel morpholine derivatives provided by this invention are morpholine compounds of the formula:

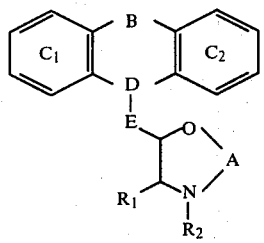

(I)

wherein $R_1$ is hydrogen or $C_1$-$C_4$ alkyl, $R_2$ is hydrogen, $C_1$-$C_4$ alkyl, $C_3$-$C_5$ alkenyl, $C_3$-$C_5$ alkynyl, aryl($C_1$-$C_4$)alkyl, ($C_3$-$C_6$)cycloalkyl($C_1$-$C_4$)alkyl, polyhalo($C_2$-$C_4$)alkyl or hydroxy($C_2$-$C_4$)alkyl, A is straight or branched $C_2$-$C_4$ alkylene, B is —CH$_2$—CH$_2$—, —CH=CH—,

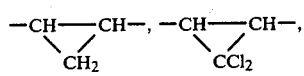

—CH$_2$—O—, —CH$_2$—S—, —S— or —O—, >D—E— is >CH—CH$_2$— or >C=CH— and $C_1$ and $C_2$ are each 1,2-phenylene optionally substituted with one or more substituents selected from the group consisting of halogen, $C_1$-$C_4$ alkyl and $C_1$-$C_4$ alkoxy, and their non-toxic salts.

In the above significances, as "$C_1$-$C_4$ alkyl", there may be exemplified methyl, ethyl, n-propyl, isopropyl, n-butyl, etc. The term "$C_3$-$C_5$ alkenyl" may include allyl, 3,3-dimethylallyl, etc. The term "$C_3$-$C_5$ alkynyl" may include propargyl, butynyl, etc. Examples of "aryl($C_1$-$C_4$)alkyl" are benzyl, phenethyl, etc. Examples of "($C_3$-$C_6$)cycloalkyl($C_1$-$C_4$)alkyl" are cyclopropylmethyl, cyclopropylethyl, etc. Examples of polyhalo($C_2$-$C_4$)alkyl" are trifluoroethyl, difluoroethyl, etc. Examples of "hydroxy($C_2$-$C_4$)alkyl" are hydroxyethyl, hydroxypropyl, etc. As "$C_1$-$C_4$ alkoxy", there may be exemplified methoxy, ethoxy, etc. The term "straight or branched $C_2$-$C_4$ alkylene" covers ethylene, propylene, isopropylene, etc. The term "halogen" may cover fluorine, chlorine, bromine, etc.

The morpholine compounds [I] may form acid addition salts (e.g. hydrochloride, hydrobromide, sulfate, acetate, oxalate, citrate, succinate, fumarate, lactate) and quaternary ammonium salts (e.g. methochloride, methiodide).

The morpholine compounds [I] and their non-toxic salts exhibit pharmacological activities and are useful as medicines. In general, they affect the functioning of the central nervous system. That is, they antagonize the central nervous system depressant effect induced by tetrabenazine and by reserpine, and also potentiate the central action of norepinephrine. Therefore, they are useful as antidepressants. Moreover, the acute toxicity and the acute cardio-toxicity of these compounds are relatively low, compared with those of standard antidepressants.

Among the morpholine compounds [I] of the invention, those of the following formula are preferable:

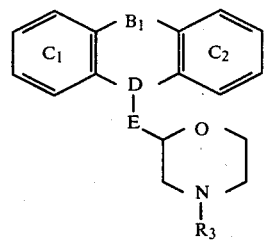

[I']

wherein $B_1$ is —CH$_2$—CH$_2$—, —CH=CH—,

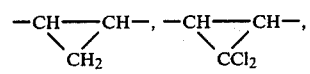

—CH$_2$—O— or —CH$_2$—S—, $R_3$ is hydrogen, $C_1$—$C_3$ alkyl, allyl, propargyl, benzyl, cyclopropylmethyl, 2,2,2-trifluoroethyl or 2-hydroxyethyl and >D—E—, $C_1$ and $C_2$ are each as defined above, and their non-toxic salts.

The compounds of the following formula are particularly preferable:

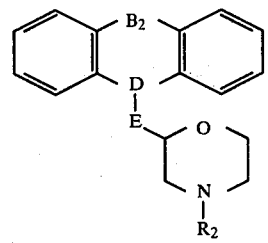

[I'']

wherein $B_2$ is —CH$_2$—CH$_2$—, —CH=CH— or

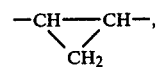

$R_4$ is hydrogen or $C_1$-$C_3$ alkyl (preferably methyl) and >D—E— is as defined above, and their non-toxic salts.

The morpholine compounds [I] and their non-toxic salts can be administered parenterally or orally with dosage adjusted to individual requirements (10–300 mg/human body (60 kg of body weight)/day) in the form of conventional pharmaceutical preparations. For instance, they may be administered in the form of a conventional solid pharmaceutical preparation such as tablets or capsules or in the form of a conventional liquid pharmaceutical preparation such as suspensions, emulsions or solutions.

The morpholine compounds [I] can be prepared, for instance, by the following methods.

(a) The morpholine compound of the formula:

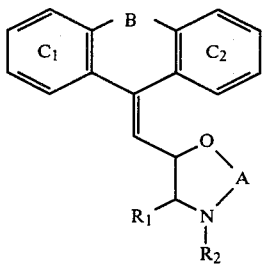

[Ia]

wherein $R_1$, $R_2$, A, B, $C_1$ and $C_2$ are each as defined above can be prepared by subjecting the allylaminoalcohol of the formula:

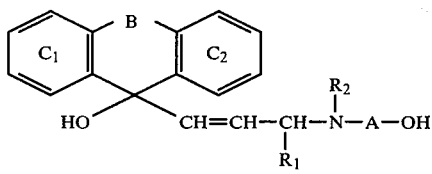

[II]

wherein $R_1$, $R_2$, A, B, $C_1$ and $C_2$ are each as defined above to acid-catalyzed rearrangement, followed by intramolecular cyclization.

The rearrangement and cyclization may be carried out by treating the compound [II] with an acid in the presence or absence of an inert solvent such as acetic acid, chloroform, n-hexane, diethyl ether or benzene. Examples of the acid are inorganic acids (e.g. hydrochloric acid, hydrobromic acid, sulfuric acid, nitric acid, phosphoric acid, polyphosphoric acid), organic strong acids (e.g. methanesulfonic acid, benzenesulfonic acid, toluenesulfonic acid, oxalic acid, formic acid, trifluoroacetic acid), Lewis acids (e.g. aluminum chloride, boron trifluoride), etc. The temperature for the treatment can be varied from ice-cooling to the refluxing temperature.

(b) The morpholine compound of the formula:

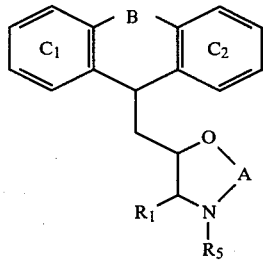

[Ib]

wherein $R_5$ is $C_1$-$C_4$ alkyl, $C_3$-$C_5$ alkenyl, $C_3$-$C_5$ alkynyl, aryl($C_1$-$C_4$)alkyl or ($C_3$-$C_6$)cycloalkyl($C_1$-$C_4$)alkyl and $R_1$, A, B, $C_1$ and $C_2$ are each as defined above can be prepared by reacting the tricyclic compound of the formula:

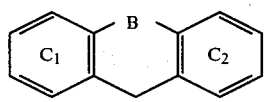

[III]

wherein B, $C_1$ and $C_2$ are each as defined above with the morpholinomethyl compound of the formula:

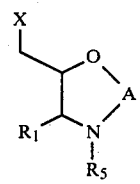

[IV]

wherein X is a conventional leaving group such as halogen (e.g. chlorine, bromine) or sulfonyloxy (e.g. —O—SO$_2$R$_{12}$ wherein R$_{12}$ is hydroxyl, $C_1$-$C_3$ alkyl, polyhalo($C_1$-$C_3$)alkyl, aryl, $C_1$-$C_3$ alkoxy or aryloxy) and $R_1$, $R_5$ and A are each as defined above.

The reaction is usually carried out in an inert solvent such as benzene, toluene, xylene, diethyl ether, tetrahydrofuran, dioxane, dimethylformamide or dimethylsulfoxide in the presence of a base such as a metal amide (e.g. sodium amide, potassium amide), a metal hydride (e.g. sodium hydride) or an alkyl or aryl metal (e.g. n-butyl lithium, phenyl lithium). The temperature for the reaction can be varied from dry-ice-cooling to the refluxing temperature.

(c) The morpholine compound of the formula:

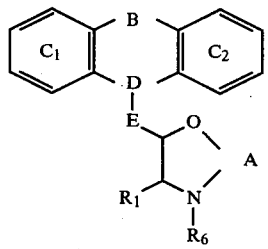

[Ic]

wherein $R_6$ is hydrogen, $C_1$-$C_4$ alkyl, $C_3$-$C_5$ alkenyl, $C_3$-$C_5$ alkynyl, aryl($C_1$-$C_4$)alkyl, ($C_3$-$C_6$)cycloalkyl($C_1$-$C_4$)alkyl or polyhalo($C_2$-$C_4$)alkyl and $R_1$, A, B, >D—E—, $C_1$ and $C_2$ are each as defined above can be prepared by reacting the epoxide of the formula:

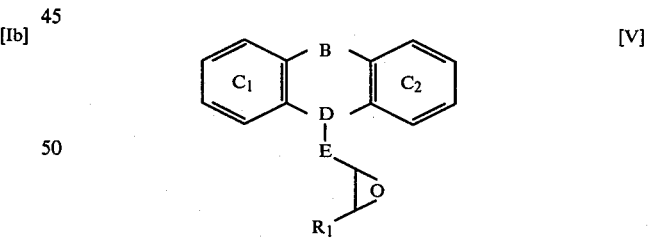

[V]

wherein $R_1$, B, >D—E—, $C_1$ and $C_2$ are each as defined above with the amine of the formula:

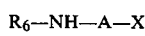

$R_6$—NH—A—X       [VI]

wherein $R_6$, A and X are each as defined above, followed by treatment with a base.

The reaction of the epoxide [V] with the amine [VI] is usually carried out in an inert solvent such as an alcohol (e.g. methanol, ethanol, isopropanol, ethyleneglycol), an ether (e.g. diethylether, tetrahydrofuran, dioxane), an aromatic hydrocarbon (e.g. benzene, toluene) or their mixture in the presence of a base such as a metal hydroxide (e.g. sodium hydroxide, potassium hydroxide, barium hydroxide) at a wide range of temperature from room temperature to the refluxing temperature of the reaction system.

As the reaction product, there is obtained the aminoalcohol of the formula:

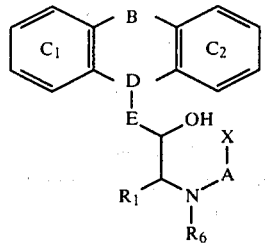 [VII]

wherein $R_1$, $R_6$, A, B, >D—E—, $C_1$, $C_2$ and X are each as defined above, which is then subjected to treatment with a base with or without the previous separation from the reaction mixture. The treatment may be carried out at a temperature from ice-cooling to the refluxing temperature of the reaction system. As the base, there may be employed a metal hydroxide (e.g. sodium hydroxide, potassium hydroxide, barium hydroxide), usually in an equimolar amount or more. The use of an inert solvent such as methanol, ethanol, tetrahydrofuran, dioxane, benzene or toluene is normally preferred.

(d) The morpholine compound of the formula:

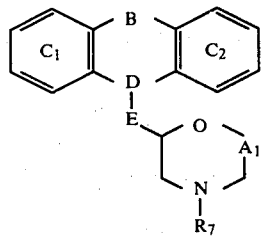 [Id]

wherein $R_7$ is hydrogen, $C_1$-$C_4$ alkyl, $C_3$-$C_5$ alkenyl, $C_3$-$C_5$ alkynyl, aryl($C_1$-$C_4$)alkyl, ($C_3$-$C_6$)cycloalkyl($C_1$-$C_4$)alkyl or hydroxy($C_2$-$C_4$)alkyl, $A_1$ is straight or branched $C_1$-$C_3$ alkylene and B, >D—E—, $C_1$ and $C_2$ are each as defined above can be prepared by reduction of the lactam of the formula:

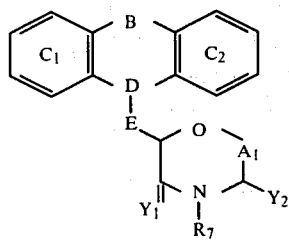 [VIII]

wherein $A_1$, B, $R_7$, >D—E—, $C_1$ and $C_2$ are each as defined above, $Y_1$ represents an oxygen atom or two hydrogen atoms and $Y_2$ represents an oxygen atom when $Y_1$ is two hydrogens or $Y_2$ represents two hydrogen atoms when $Y_1$ is oxygen.

The reduction may be accomplished by the use of a reducing agent which is conventionally employed for reduction of a lactam

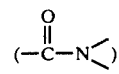

to an amine (—$CH_2$—N<). One of the most preferred reducing agents is a metal hydride such as lithium aluminum hydride, sodium bis(2-methoxyethoxy)-aluminum hydride or sodium dihydrodiethyl aluminate. The reducing agent can be used in an equimolar amount or more with respect to the compound [VIII]. In case of using sodium borohydride as the reducing agent, the presence of a salt such as aluminum chloride is favored. When desired, an inert solvent such as an ether (e.g. diethyl ether, tetrahydrofuran, dioxane, ethyleneglycol dimethyl ether), an aliphatic hydrocarbon (e.g. heptane, n-hexane, cyclohexane) or an aromatic hydrocarbon (e.g. benzene, toluene) may be employed in the reduction. The temperature for the reduction can be varied from ice-cooling to the refluxing temperature of the reduction system.

(e) The morpholine compound of the formula:

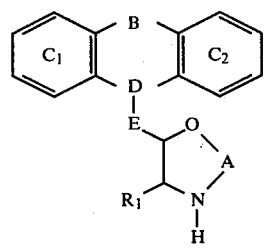 [Ie]

wherein $R_1$, A, B, >D—E—, $C_1$ and $C_2$ are each as defined above can be prepared from the morpholine compound of the formula:

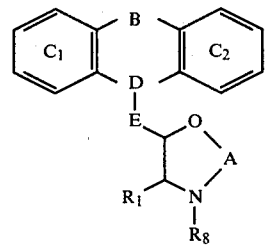 [IX]

wherein $R_8$ is $C_1$-$C_4$ alkyl or aryl($C_1$-$C_4$)alkyl and $R_1$, A, B, >D—E—, $C_1$ and $C_2$ are each as defined above by substitution of $R_8$ with hydrogen.

One of the most useful procedures for the substitution is the reaction of the compound [IX] with an alkyl or aryl chloroformate (e.g. methyl chloroformate, ethyl chloroformate, phenyl chloroformate), followed by hydrolysis of the resulting alkoxycarbonyl or aryloxycarbonyl compound. The reaction with the alkyl or aryl chloroformate may be performed at a temperature of from room temperature to the refluxing temperature in an inert solvent (e.g. benzen, toluene). The hydrolysis of the resulting alkoxycarbonyl or aryloxycarbonyl compound is usually carried out in an inert solvent (e.g. water, hydrous methanol, hydrous ethanol) in the presence of a base such as a metal hydroxide (e.g. sodium hydroxide, potassium hydroxide) at a temperature of from room temperature to the refluxing temperature.

Another useful procedure for the substitution which is particularly applicable to the production of the compound [Ie] wherein B is other than —CH═CH— from the corresponding compound [IX] wherein $R_8$ is benzyl is catalytic hydrogenation. The catalytic hydrogenolysis may be carried out in the presence of a catalyst such as palladium-on-charcoal under an atmosphere of hydrogen gas in an inert solvent such as an alcohol (e.g. methanol, ethanol). The hydrogen pressure can be 1 atmospheric pressure or higher, and the temperature may be room temperature or higher. The presence of an acid (e.g. hydrochloric acid, acetic acid) in the reduction system may promote the progress of the reaction.

The compound [Ie] wherein B is —CH$_2$—CH$_2$— can also be prepared by catalytic hydrogenation and hydrogenolysis of the compound [IX] wherein B is —CH═CH— and $R_8$ is benzyl under the same condition as above.

(f) The morpholine compound of the formula:

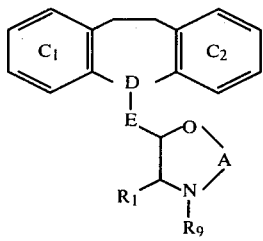

(If)

wherein $R_9$ is hydrogen, $C_1$-$C_4$ alkyl, aryl($C_1$-$C_4$) alkyl, ($C_3$-$C_6$)cycloalkyl($C_1$-$C_4$)alkyl, polyhalo($C_2$-$C_4$)alkyl or hydroxy($C_2$-$C_4$)alkyl and $R_1$, A, >D-E-, $C_1$ and $C_2$ are each as defined above can be prepared by catalytic hydrogenation of the morpholine compound of the formula:

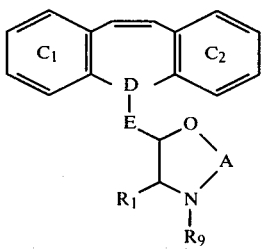

[X]

wherein $R_1$, A, >D-E-, $R_9$, $C_1$ and $C_2$ are each as defined above.

The catalytic hydrogenation may be carried out in the presence of a catalyst such as palladium-on-charcoal under an atmosphere of hydrogen gas in an inert solvent such as an alcohol (e.g. methanol, ethanol). The hydrogen pressure can be 1 atmospheric pressure or higher, and the temperature may be room temperature or higher.

(g) The morpholine compound of the formula:

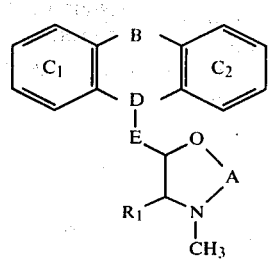

[Ig]

wherein $R_1$, A, B, >D-E-, $C_1$ and $C_2$ are each as defined above can be prepared by reducing the morpholine compound of the formula:

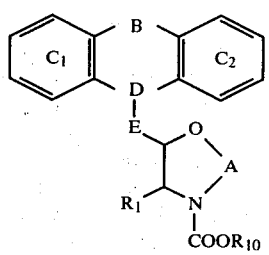

[XI]

wherein $R_{10}$ is $C_1$-$C_4$ alkyl or aryl and $R_1$, A, B, >D-E-, $C_1$ and $C_2$ are each as defined above. The reduction may be carried out in the substantially same manner as in Method (d).

(h) The morpholine compound of the formula:

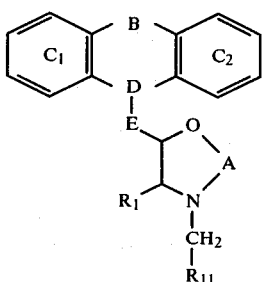

[Ih]

wherein $R_{11}$ is hydrogen, $C_1$-$C_3$ alkyl, $C_2$-$C_4$ alkenyl, $C_2$-$C_4$ alkynyl, ($C_3$-$C_6$)cycloalkyl($C_1$-$C_3$)alkyl, ($C_3$-$C_6$)cycloalkyl, aryl($C_1$-$C_3$)alkyl, hydroxy($C_1$-$C_3$)alkyl or aryl and $R_1$, A, B, >D-E-, $C_1$ and $C_2$ are each as defined above can be prepared by reducing the morpholine compound of the formula:

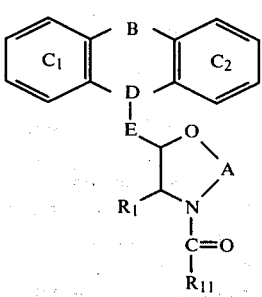

[XII]

wherein $R_1$, A, B, >D-E-, $R_{11}$, $C_1$ and $C_2$ are each as defined above. The reduction may be carried out in the substantially same manner as in Method (d).

(i) The morpholine compound of the formula:

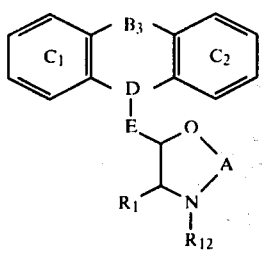
[Ii]

wherein $R_{12}$ is $C_1$-$C_4$ alkyl, $C_3$-$C_5$ alkenyl, $C_3$-$C_5$ alkynyl, aryl($C_1$-$C_4$)alkyl, ($C_3$-$C_6$)cycloalkyl($C_1$-$C_4$)alkyl, polyhalo($C_2$-$C_4$)alkyl or hydroxy($C_2$-$C_4$) alkyl, $B_3$ is —$CH_2$—$CH_2$—, —CH=CH—,

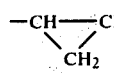

—$CH_2$—O—, —$CH_2$—S—, —S— or —O— and $R_1$, A, >D-E-, $C_1$ and $C_2$ are each as defined above can be prepared by condensation of the morpholine compound of the formula:

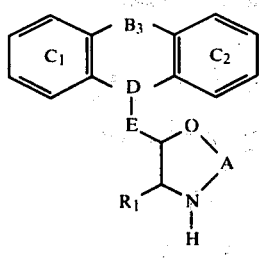
[XIII]

wherein $R_1$, A, $B_3$, >D-E-, $C_1$ and $C_2$ are each as defined above with a compound of the formula:

Z-$R_{12}$      [XIV]

wherein Z is a conventional leaving group such as halogen (e.g. chlorine, bromine) or sulfonyloxy (e.g. methanesulfonyloxy, p-toluenesulfonyloxy, trichloromethanesulfonyloxy) and $R_{12}$ is as defined above.

The condensation may be effected in an inert solvent such as an aromatic hydrocarbon (e.g. benzene, toluene, xylene), dimethylformamide, dimethylsulfoxide or an alcohol (e.g. methanol, ethanol, propanol) in the presence of a base. Examples of the base are a metal carbonate (e.g. sodium carbonate, potassium carbonate), a metal bicarbonate (e.g. sodium bicarbonate, potassium bicarbonate), a metal hydroxide (e.g. sodium hydroxide, potassium hydroxide), a metal hydride (e.g. sodium hydride, potassium hydride), an alkylamine (e.g. triethylamine) or a metal alkoxide (e.g. sodium methoxide, sodium ethoxide). The base may be used in a stoichiometric amount or more. The temperature for the condensation can be varied from room temperature to the refluxing temperature.

(j) The morpholine compound [Ih] can be prepared by condensation-reduction of the corresponding morpholine compound [Ie] with a carbonyl compound of the formula:

$$R_{11}-\overset{O}{\overset{\|}{C}}-H \qquad [XV]$$

wherein $R_{11}$ is as defined above.

The condensation-reduction may be accomplished by per se known procedures. The usual procedure of the Leuckart-Wallach reaction using formic acid is applicable to the condensation-reduction [Organic Reactions, Vol. 5, p. 301, John Wiley & Sons, Inc.]. For instance, the compound [XV] is added to a mixture of the amine-formate of the compound [Ie] and formic acid, and the resultant mixture is heated at a temperature from room temperature to 200° C.

the condensation-reduction can be also accomplished by hydrogenation of a mixture of the compound [Ie] and the compound [XV] over a catalyst such as Raney nickel, platinum oxide or palladium in the presence or absence of an inert solvent. The pressure may be 1 atmospheric pressure or higher. A condensation agent such as sodium acetate may be used.

The condensation-reduction can be further accomplished by using the sodium-alcohol or zinc-acid or alkali method. Examples of an inert solvent utilizable in the reaction are alcohols (e.g. methanol, ethanol, isopropanol), liquid ammonia, acetic acid and ethers (e.g. diethyl ether, diisopropyl ether, tetrahydrofuran, dioxane).

Moreover, the condensation-reduction can be accomplished by the reduction of the Schiff base or enamine prepared from the compound [Ie] and the compound [XV] in a conventional procedure. The reduction may be performed in the same manner as the hydrogenation procedure described above. A reducing agent such as sodium borohydride, diborane, lithium aluminum hydride, sodium aluminum diethyldihydride, sodium borocyanohydride or bis(2-methoxyethoxy)-aluminum hydride can be used in the reduction in an inert solvent such as an alcohol (e.g. methanol, ethanol, isopropanol, n-butanol, t-butanol), an aromatic hydrocarbon (e.g. benzene, toluene) or an ether (e.g. diethyl ether, diisopropyl ether, dioxane, tetrahydrofuran). The temperature for the treatment in this case can be varied from —10° C. to the refluxing temperature.

The thus prepared morpholine compounds [I] can be converted into their salts by a conventional procedure, and reconversion from the salts to the original free bases can be also carried out in a conventional manner.

The intermediate tricyclic allylaminoalcohol [II], for example, can be prepared from the tricyclic carbonyl compound of the formula:

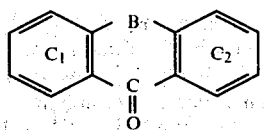
[XVI]

wherein B, $C_1$ and $C_2$ are each as defined above according to the following steps:

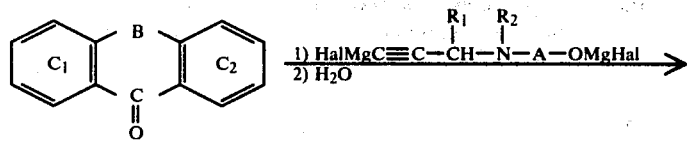

[XVI]

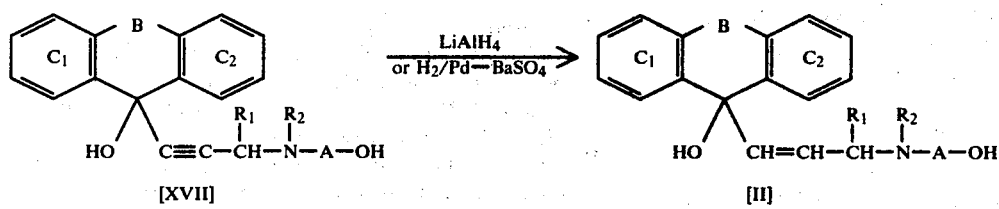

[XVII]    [II]

wherein Hal is halogen (e.g. chlorine, bromine, iodine) and $R_1$, $R_2$, A, B, $C_1$ and $C_2$ are each as defined above.

The first step is the Grignard reaction of the tricyclic carbonyl compound [XVI] with an acetylenic Grignard reagent in an inert solvent. The second step is the partial reduction of the resulting tricyclic propargylaminoalcohol [XVII] with a metal hydride such as lithium aluminum hydride or hydrogen in the presence of a metal catalyst such as palladium on barium sulfate.

The intermediate epoxide [V], for example, can be prepared by the known method [Dutch Patent Application No. 66.05979].

The intermediate lactam [VIII], for example, can be prepared from the epoxide [V] wherein $R_1$ is hydrogen, according to the following steps:

tion of the resulting amide [XXI] in the presence of an acid.

The lactam [VIII] wherein $Y_1$ is an oxygen atom and $Y_2$ is two hydrogen atoms, for example, can be prepared from the epoxide [V] via the aldehyde [XVIII], the carboxylic acid [XIX] and the amide [XX]. The first step is the isomerization of the epoxide [V] in the presence of an acid such as boron trifluoride-etherate. The second step is the halogenation of the carboxylic acid [XIX] followed by the amidation of the resulting halocarboxylic acid. The third step is the intramolecular dehydrohalogenation of the halo-amide [XX] in the presence of a base.

The following examples are given to illustrate the present invention more precisely.

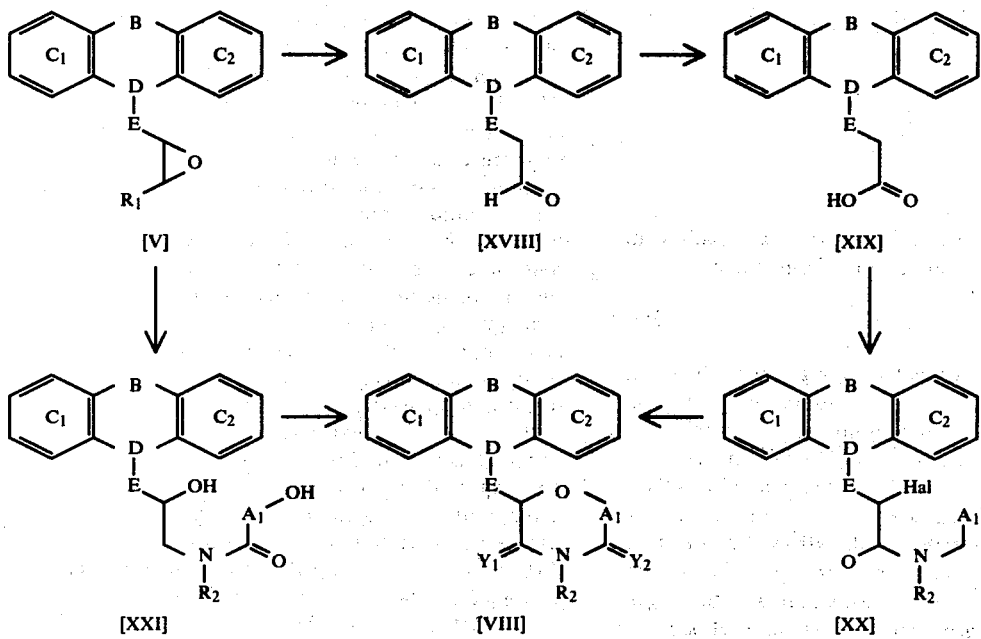

wherein $R_1$ is hydrogen and $R_2$, $A_1$, B, >D-E-, $C_1$, $C_2$, $Y_1$, $Y_2$ and Hal are each as defined above.

The lactam [VIII] wherein $Y_1$ is two hydrogen atoms and $Y_2$ is an oxygen atom, for example, can be prepared from the epoxide [V] via the amide [XXI]. The first step is the amination of the epoxide [V], followed by acylation of the resulting aminoalcohol with an acylating agent. The second step is the intramolecular dehydra-

EXAMPLE 1

Concentrated hydrochloric acid (7 ml) was added to a solution of N-benzyl-N-[3-(10,11-dihydro-5H-dibenzo[a,d]-cyclohepten-5-yl)allyl]-2-ethanolamine (498 mg) in glacial acetic acid under ice-cooling, and the resulting mixture was stirred at room temperature for 4 hours. After the reaction mixture was evaporated to dryness under reduced pressure, the residue was neutralized with 10% aqueous sodium hydroxide solution and extracted with chloroform. The chloroform extract was dried over anhydrous sodium sulfate and evaporated to afford 5-(4-benzylmorpholin-2-yl)methylidene-10,11-dihydro-5H-dibenzo[a,d]cycloheptene as oily material. M.P., 209°–210° C. (decomp.) (oxalate).

EXAMPLE 2

A solution of n-butyl lithium in n-hexane (1.6 N, 1.6 ml) was added to 10,11-dihydro-5H-dibenzo[a,d]cycloheptene (390 mg) in anhydrous tetrahydrofuran at room temperature, and the resulting mixture was stirred under reflux for 40 minutes. A solution of 2-chloromethyl-4-isopropylmorpholine (362 mg) in benzene was added thereto while stirring under heating, and the resulting mixture was stirred under reflux for 4 hours, followed by addition of excess water. The reaction mixture was extracted with ethyl acetate. The ethyl acetate extract was dried, evaporated and chromatographed to afford 5-(4-isopropylmorpholin-2-yl)methyl-10,11-dihydro-5H-dibenzo[a,d]cycloheptene as oily material. M.P., 219°–221° C. (hydrochloride).

EXAMPLE 3

Ethyl chloroformate (3.6 g) was added to 5-(4-benzylmorpholin-2-yl)methylidene-10,11-dihydro-5H-dibenzo[a,d]cycloheptene (3.13 g) in anhydrous benzene at room temperature, and the resulting mixture was heated under reflux for 5.5 hours. After cooling, the mixture was washed with a saturated aqueous sodium bicarbonate solution and water, dried and evaporated to afford 5-(4-ethoxycarbonylmorpholin-2-yl)methylidene-10,11-dihydro-5H-dibenzo[a,d]-cycloheptene as oily material.

Potassium hydroxide (3.0 g) in water was added to the above-obtained 5-(4-ethoxycarbonylmorpholin-2-yl)methylidene-10,11-dihydro-5H-dibenzo[a,d]cycloheptene (2.49 g) in ethanol, and the resulting mixture was heated under reflux for 8 hours. After cooling, ethanol was distilled off and water was added to the resulting residue. The resultant mixture was extracted with chloroform. The chloroform extract was dried, evaporated and chromatographed to afford 5-(morpholin-2-yl)methylidene-10,11-dihydro-5H-dibenzo[a,d]cycloheptene as oily material. M.P., 221°–224° C. (oxalate).

EXAMPLE 4

A solution of 5-(4-benzylmorpholin-2-yl)methylidene-10,11-dihydro-5H-dibenzo[a,d]cycloheptene (1.00 g) in isopropanol was added to 10% palladium on charcoal (265 mg) pretreated under hydrogen in hydrochloric acid, and the resulting mixture was stirred under hydrogen at room temperature for 12 hours. After elimination of the catalyst by filtration, the filtrate was evaporated. The residue was neutralized with 10% aqueous sodium hydroxide solution and extracted with chloroform. The chloroform extract was washed with water, dried and evaporated to afford 5-(morpholin-2-yl)methylidene-10,11-dihydro-5H-dibenzo[a,d]-cycloheptene as oily material. M.P., 221°–224° C. (oxalate).

EXAMPLE 5

A solution of 5-(4-benzylmorpholin-2-yl)methylidene-5H-dibenzo[a,d]cycloheptene (0.32 g) in acetic acid was added to 10% palladium on charcoal (90 mg) pretreated under hydrogen in hydrochloric acid, and the resulting mixture was stirred under hydrogen at room temperature for 8 hours. After elimination of the catalyst by filtration, the filtrate was evaporated. The residue was neutralized with 10% aqueous sodium hydroxide solution and extracted with chloroform. The chloroform extract was washed with water, dried and evaporated to afford 5-(morpholin-2-yl)methylidene-10,11-dihydro-5H-dibenzo[a,d]cycloheptene as oily material. M.P., 221°–224° (oxalate).

EXAMPLE 6

A solution of 5-(morpholin-2-yl)methylidene-5H-dibenzo[a,d]cycloheptene (0.62 g) in methanol was added to 5% palladium on charcoal (400 mg) pretreated under hydrogen in methanol, and the resulting mixture was stirred under hydrogen at room temperature for 20 hours. After elimination of the catalyst by filtration, the filtrate was evaporated to afford 5-(morpholin-2-yl)methylidene-10,11-dihydro[a,d]cycloheptene as oily material. M.P., 221°–224° C. (oxalate).

EXAMPLE 7

To a solution of lithium aluninum hydride (155 mg) in anhydrous ether was added a solution of 5-(4-ethoxycarbonylmorpholin-2-yl)methylidene-10,11-dihydro-5H-dibenzo[a,d]-cycloheptene (600 mg) in anhydrous ether under ice-cooling, and the resulting mixture was stirred under ice-cooling for 1 hour and under reflux for 2.5 hours. The reaction mixture was cooled, admixed with 10% aqueous sodium hydroxide solution and extracted with ether. The ether extract was dried over anhydrous sodium sulfate and evaporated to afford 5-(4-methylmorpholin-2-yl)methylidene-10,11-dihydro-5H-dibenzo[a,d]cycloheptene as oily material. M.P., 243°–244° C. (decomp.) (oxalate).

EXAMPLE 8

To a solution of lithium aluminum hydride (100 mg) in anhydrous ether was added a solution of 5-(4-acetylmorpholin-2-yl)methylidene-10,11-dihydro-5H-dibenzo[a,d]-cycloheptene (350 mg) in anhydrous ether under ice-cooling, and the resulting mixture was stirred under reflux for 3 hours. The reaction mixture was cooled, admixed with 10% aqueous sodium hydroxide solution and extracted with ether. The ether extract was dried over anhydrous sodium sulfate and evaporated to afford 5-(4-ethylmorpholin-2-yl)methylidene-10,11-dihydro-5H-dibenzo[a,d]cycloheptene as oily material. M.P., 224°–225° C. (oxalate).

EXAMPLE 9

To 5-(morpholin-2-yl)methylidene-10,11-dihydro-5H-dibenzo[a,d]cycloheptene (300 mg) in ethanol were added propargyl bromide (2.0 g) and potassium hydroxide (570 mg) in water at room temperature, and the resulting mixture was stirred at room temperature for 1 hour. After ethanol was distilled off, water was added to the residue, and the resultant mixture was extracted with chloroform. The chloroform extract was dried, evaporated and chromatographed to afford 5-(4-propargylmorpholin-2-yl)methylidene-10,11-dihydro-5H-dibenzo[a,d]cycloheptene as crystalline material. M.P., 124°–125° C.

EXAMPLE 10

To 5-(morpholin-2-yl)methylidene-10,11-dihydro-5H-dibenzo[a,d]cycloheptene (0.69 g) in anhydrous tetrahydrofuran was added sodium amide (0.20 g) at room temperature, and the resulting mixture was heated under reflux for 1.5 hours. After cooling, 2,2,2-trifluoroethyl trichloromethylsulfonate (0.666 g) in anhydrous tetrahydrofuran was added to the mixture under ice-cooling, and then the mixture was heated under reflux for 11.5 hours. After cooling, water (0.2 g) was added thereto and inorganic materials were eliminated by filtration. The filtrate was evaporated and chromatographed to afford 5-[4-(2,2,2-trifluoroethyl)morpholin-2-yl]methylidene-10,11-dihydro-5H-dibenzo[a,d]cycloheptene as oily material. M.P., 174°–177° C. (hydrochloride).

EXAMPLE 11

A mixture of 5-(morpholin-2-yl)methylidene-5H-dibenzo[a,d]cycloheptene (0.35 g), 90% formic acid (0.7 g) and 37% formalin (0.65 ml) was stirred at 95°–100° C. for 6.5 hours. After cooling, 4 N hydrochloric acid was added thereto, and the resulting mixture was evaporated to dryness under reduced pressure, neutralized with ammonia water and extracted with benzene. The benzene extract was washed with water, dried over anhydrous sodium sulfate and evaporated to afford 5-(4-methylmorpholin-2-yl)methylidene-5H-dibenzo[a,d]cycloheptene as oily material. M.P., 237°–238° C. (decomp.) (oxalate).

EXAMPLE 12

To a suspension of lithium aluminum hydride (0.05 g) in anhydrous tetrahydrofuran (7 ml) was added a solution of 5-(4-benzyl-5-oxomorpholin-2-yl)methylidene-10,11-dihydro-5H-dibenzo[a,d]cycloheptene (0.55 g) in anhydrous tetrahydrofuran (15 ml) under ice-cooling, and the resulting mixture was stirred at room temperature for one hour and refluxed with stirring for 7 hours. The reaction mixture was cooled, admixed with water and extracted with ether. The ether extract was dried over anhydrous sodium sulfate and evaporated to afford 5-(4-benzylmorpholin-2-yl)methylidene-10,11-dihydro-5H-dibenzo[a,d]cycloheptene as oily material. M.P., 209°–210° C. (decomp.) (oxalate).

EXAMPLE 13

A mixture of 5-(2,3-epoxypropylidene)-10,11-dihydro-5H--dibenzo[a,d]cycloheptene (0.65 g), 2-aminoethyl hydrogensulfate (2.5 g) and sodium hydroxide (1.6 g) in water (8 ml) was stirred in ethanol (11 ml) under reflux for 15 hours. The reaction mixture was concentrated and extracted with chloroform. The chloroform extract was washed with water, dried over anhydrous sodium sulfate and evaporated to afford 5-(morpholin-2-yl)methylidene-10,11-dihydro-5H-dibenzo[a,d]cycloheptene as oily material. M.P., 221°–224° C. (oxalate).

The following compounds were produced by one or more of the procedures described above:

5-(Morpholin-2-yl)methylidene-10,11-dihydro-5H-dibenzo[a,d]cycloheptene, M.P., 221°–224° C. (oxalate);

5-(Morpholin-2-yl)methyl-10,11-dihydro-5H-dibenzo[a,d]cycloheptene, M.P., 205°–207° C. (hydrochloride);

5-(4-Methylmorpholin-2-yl)methylidene-10,11-dihydro-5H-dibenzo[a,d]cycloheptene, M.P., 243°–244° C. (decomp.) (oxalate);

5-(4-Methylmorpholin-2-yl)methyl-10,11-dihydro-5H-dibenzo[a,d]cycloheptene, M.P., 188°–189.5° C. (hydrochloride);

5-(4-Benzylmorpholin-2-yl)methylidene-10,11-dihydro-5H-dibenzo[a,d]cycloheptene, M.P., 209°–210° C. (decomp.) (oxalate);

5-(4-Benzylmorpholin-2-yl)methyl-10,11-dihydro-5H-dibenzo[a,d]cycloheptene, M.P., 128°–131° C. (hydrochloride);

5-(4-Ethylmorpholin-2-yl)methylidene-10,11-dihydro-5H-dibenzo[a,d]cycloheptene, M.P., 224°–225° C. (decomp.) (oxalate);

5-(4-Cyclopropylmethylmorpholin-2-yl)methylidene-10,11-dihydro-5H-dibenzo[a,d]cycloheptene, M.P., 195°–198° C. (hydrochloride);

5-(4-Isopropylmorpholin-2-yl)methyl-10,11-dihydro-5H-dibenzo[a,d]cycloheptene, M.P., 219°–221° C. (hydrochloride);

5-(4-Allylmorpholin-2-yl)methylidene-10,11-dihydro-5H-dibenzo[a,d]cycloheptene, M.P., 212°–213° C. (decomp.) (oxalate);

5-(4-Propargylmorpholin-2-yl)methylidene-10,11-dihydro-5H-dibenzo[a,d]cycloheptene, M.P., 124°–125° C.;

5-[4-(2-Hydroxyethyl)morpholin-2-yl]methylidene-10,11-dihydro-5H-dibenzo[a,d]cycloheptene, M.P., 210°–212° C. (hydrochloride);

5-[4-(2,2,2-Trifluoroethyl)morpholin-2-yl]methylidene-10,11-dihydro-5H-dibenzo[a,d]cycloheptene, M.P., 174°–177° C. (hydrochloride);

5-(Morpholin-2-yl)methylidene-5H-dibenzo[a,d]cycloheptene, M.P., 224°–226° C. (decomp.) (oxalate);

5-(Morpholin-2-yl)methyl-5H-dibenzo[a,d]cycloheptene, M.P., 198.5°–200° C. (oxalate);

5-(4-Methylmorpholin-2-yl)methylidene-5H-dibenzo[a,d]cycloheptene, M.P., 237°–238° C. (decomp.) (oxalate);

5-(4-Benzylmorpholin-2-yl)methyl-5H-dibenzo[a,d]cycloheptene, I.R. (neat): 3060, 3030, 1595, 1492, 1480, 1350, 1065, 1035, 850, 800, 765 and 700 cm$^{-1}$;

5-(4-Isopropylmorpholin-2-yl)methyl-5H-dibenzo[a,d]cycloheptene, M.P., 166°–169° C. (hydrochloride);

5-(4-Propargylmorpholin-2-yl)methylidene-5H-dibenzo[a,d]cycloheptene, M.P., 146°–150° C. (hydrochloride);

6-(Morpholin-2-yl)methylidene-1,1a,6,10b-tetrahydrodibenzo[a,e]cyclopropa[c]cycloheptene, M.P., 163°–165° C. (hydrochloride);

6-(4-Methylmorpholin-2-yl)methylidene-1,1a,6,10b-tetrahydrodibenzo[a,e]cyclopropa[c]cycloheptene, M.P., 235°–236° C. (decomp.) (oxalate);

6-(4-Benzylmorpholin-2-yl)methylidene-1,1a,6,10b-tetrahydrodibenzo[a,e]cyclopropa[c]cycloheptene, M.P., 151°–154° C. (hydrochloride);

6-(4-Isopropylmorpholin-2-yl)methyl-1,1a,6,10b-tetrahydrodibenzo[a,e]cyclopropa[c]cycloheptene, M.P., 162°–165° C. (hydrochloride);

1,1-Dichloro-6-(4-benzylmorpholin-2-yl)methylidene-1,1a,6,10b-tetrahydrodibenzo[a,e]cyclopropa[c]cycloheptene, I.R. (neat): 3060, 3020, 1650, 1600, 1570, 1490, 1455, 1100, 1065, 1020 and 745 cm$^{-1}$;

11-(Morpholin-2-yl)methylidene-6,11-dihydrodibenzo[b,e]oxepin, M.P., 207°–210° C. (oxalate);

11-(4-Methylmorpholin-2-yl)methylidene-6,11-dihydrodibenzo[b,e]oxepin, M.P., 120°–121° C. (oxalate);

11-(4-Benzylmorpholin-2-yl)methylidene-6,11-dihydrodibenzo[b,e]oxepin, M.P., 153°–155° C. (decomp.) (oxalate);

11-(4-Methylmorpholin-2-yl)methylidene-6,11-dihydrodibenzo[b,e]thiepine, M.P., 122°–123° C. (oxalate);

9-(Morpholin-2-yl)methylxanthene, M.P., 200°-201° C. (oxalate);

9-(4-Benzylmorpholin-2-yl)methylxanthene, I.R. (neat): 3060, 3020, 1605, 1585, 1485, 1465, 1115 and 765 cm$^{-1}$;

2-Chloro-9-(4-methylmorpholin-2-yl)methylidenethioxanthene, I.R. (neat): 3050, 3000, 2780, 1620, 1580, 1555, 1540, 1450, 1105, 1095, 1065 and 750 cm$^{-1}$;

9-(4-Isopropylmorpholin-2-yl)methylthioxanthene, M.P., 225°-225.5° C. (hydrochloride);

5-(Hexahydro-4-methyl-1,4-oxazepin-2-yl)methylidene-10,11-dihydro-5H-dibenzo[a,d]cycloheptene, M.P., 188°-190° C. (oxalate);

6-(4-Benzylmorpholin-2-yl)methyl-1,1a,6,10b-tetrahydrodibenzo[a,e]cyclopropa[c]cycloheptene, M.P., 123°-125° C.;

6-(Morpholin-2-yl)methyl-1,1a,6,10b-tetrahydrodibenzo[a,e]cyclopropa[c]cycloheptene, M.P., 203°-205° C. (oxalate), etc.

Examples of other typical tricyclic morpholine derivatives provided by the invention are as follows:

5-(4-Isopropylmorpholin-2-yl)methylidene-10,11-dihydro-5H-dibenzo[a,d]cycloheptene;

5-(4-Methylmorpholin-2-yl)methyl-5H-dibenzo[a,d]cycloheptene;

6-(Morpholin-2-yl)methyl-1,1a,6,10b-tetrahydrodibenzo[a,e]cyclopropa[c]cycloheptene;

6-(4-Methylmorpholin-2-yl)methyl-1,1a,6,10b-tetrahydrodibenzo[a,e]cyclopropa[c]cycloheptene;

11-(Morpholin-2-yl)methyl-6,11-dihydrodibenzo[b,e]oxepin;

11-(4-Methylmorpholin-2-yl)methyl-6,11-dihydrodibenzo[b,e]oxepin;

11-(Morpholin-2-yl)methylidene-6,11-dihydrodibenzo[b,e]thiepin;

11-(Morpholin-2-yl)methyl-6,11-dihydrodibenzo[b,e]thiepin;

11-(4-Methylmorpholin-2-yl)methyl-6,11-dihydrodibenzo[b,e]thiepin;

9-(Morpholin-2-yl)methylidenexanthene;

9-(Morpholin-2-yl)methylidenethioxanthene;

5-(3-Methylmorpholin-2-yl)methylidene-10,11-dihydro-5H-dibenzo[a,d]cycloheptene;

5-(5-Methylmorpholin-2-yl)methylidene-10,11-dihydro-5H-dibenzo[a,d]cycloheptene;

5-(6-Methylmorpholin-2-yl)methylidene-5H-dibenzo[a,d]cycloheptene;

5-[4-(3,3-Dimethylallyl)morpholin-2-yl]methylidene-10,11-dihydro-5H-dibenzo[a,d]cycloheptene;

1,1-Dichloro-6-(morpholin-2-yl)methylidene-1,1a,6,10b-tetrahydrodibenzo[a,e]cyclopropa[c]cycloheptene;

1,1-Dichloro-6-(4-methylmorpholin-2-yl)methylidene-1,1a,6,10b-tetrahydrodibenzo[a,e]cyclopropa[c]cycloheptene, etc.

What is claimed is:

1. A compound of the formula:

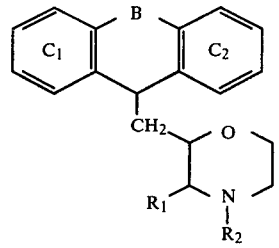

wherein $R_1$ is hydrogen or $C_1$-$C_4$ alkyl, $R_2$ is hydrogen, $C_1$-$C_4$ alkyl, $C_3$-$C_5$ alkenyl, $C_3$-$C_5$ alkynyl, phenyl($C_1$-$C_4$)alkyl, ($C_3$-$C_6$)cycloalkyl($C_1$-$C_4$)alkyl, trifluoroethyl- or difluoroethyl($C_2$-$C_4$)alkyl or hydroxy($C_2$-$C_4$)alkyl, B is —CH$_2$—CH$_2$—, —CH=CH—,

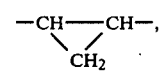

or

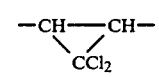

and $C_1$ and $C_2$ are each unsubstituted 1,2-phenylene or 1,2-phenylene substituted with one or more substituents selected from the group consisting of halogen, $C_1$-$C_4$ alkyl and $C_1$-$C_4$ alkoxy, or a non-toxic salt thereof.

2. The compound according to claim 1, wherein $R_1$ is hydrogen, B is —CH$_2$—CH$_2$—, —CH=CH—,

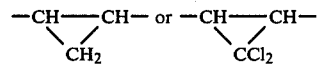

and $R_2$ is hydrogen, $C_1$-$C_3$ alkyl, allyl, propargyl, benzyl, cyclopropylmethyl, 2,2,2-trifluoroethyl or 2-hydroxyethyl, or a non-toxic salt thereof.

3. The compound according to claim 1, wherein B is —CH$_2$—CH$_2$—, —CH=CH— or

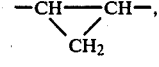

$R_2$ is hydrogen or $C_1$-$C_3$ alkyl and $C_1$ and $C_2$ are each unsubstituted 1,2-phenylene, or a non-toxic salt thereof.

4. The compound according to claim 1, wherein $R_2$ is hydrogen or methyl, or a non-toxic salt thereof.

5. The compound 5-(morpholin-2-yl)methyl-10,11-dihydro-5H-dibenzo[a,d]cycloheptene, or a non-toxic salt thereof.

6. The compound 5-(4-methylmorpholin-2-yl)methyl-10,11-dihydro-5H-dibenzo[a,d]cycloheptene, or a non-toxic salt thereof.

7. The compound 5-(morpholin-2-yl)methyl-5H-dibenzo[a,d] cycloheptene, or a non-toxic salt thereof.

8. An antidepressant pharmaceutical composition comprising an effective antidepressant amount of at least one morpholine compound according to claim 1 as an active ingredient, and a pharmaceutically acceptable carrier or diluent.

9. A method for the treatment of mental depression which comprises administering an effective antidepressant amount of the compound of claim 1 to a human.

10. The method according to claim 9, wherein the amount of morpholine compound administered per day is from 10 to 300 mg. per 60 kg. of body weight.

* * * * *

UNITED STATES PATENT AND TRADEMARK OFFICE
CERTIFICATE OF CORRECTION

PATENT NO. : 4,169,146
DATED : Sep. 25, 1979
INVENTOR(S) : Katsube et al

It is certified that error appears in the above-identified patent and that said Letters Patent are hereby corrected as shown below:

In the Section entitled "Foreign Application Priority Data",

Change "Jun. 1, 1975 [JP] Japan..........50-4540" to --Jan. 6, 1975 [JP] Japan.........50-4540--

Signed and Sealed this

*Fifteenth* Day of *July 1980*

[SEAL]

*Attest:*

SIDNEY A. DIAMOND

*Attesting Officer*  *Commissioner of Patents and Trademarks*